Dec. 23, 1969 D. L. ARMSTRONG Plant Pat. 2,958
NECTARINE TREE
Filed May 28, 1968
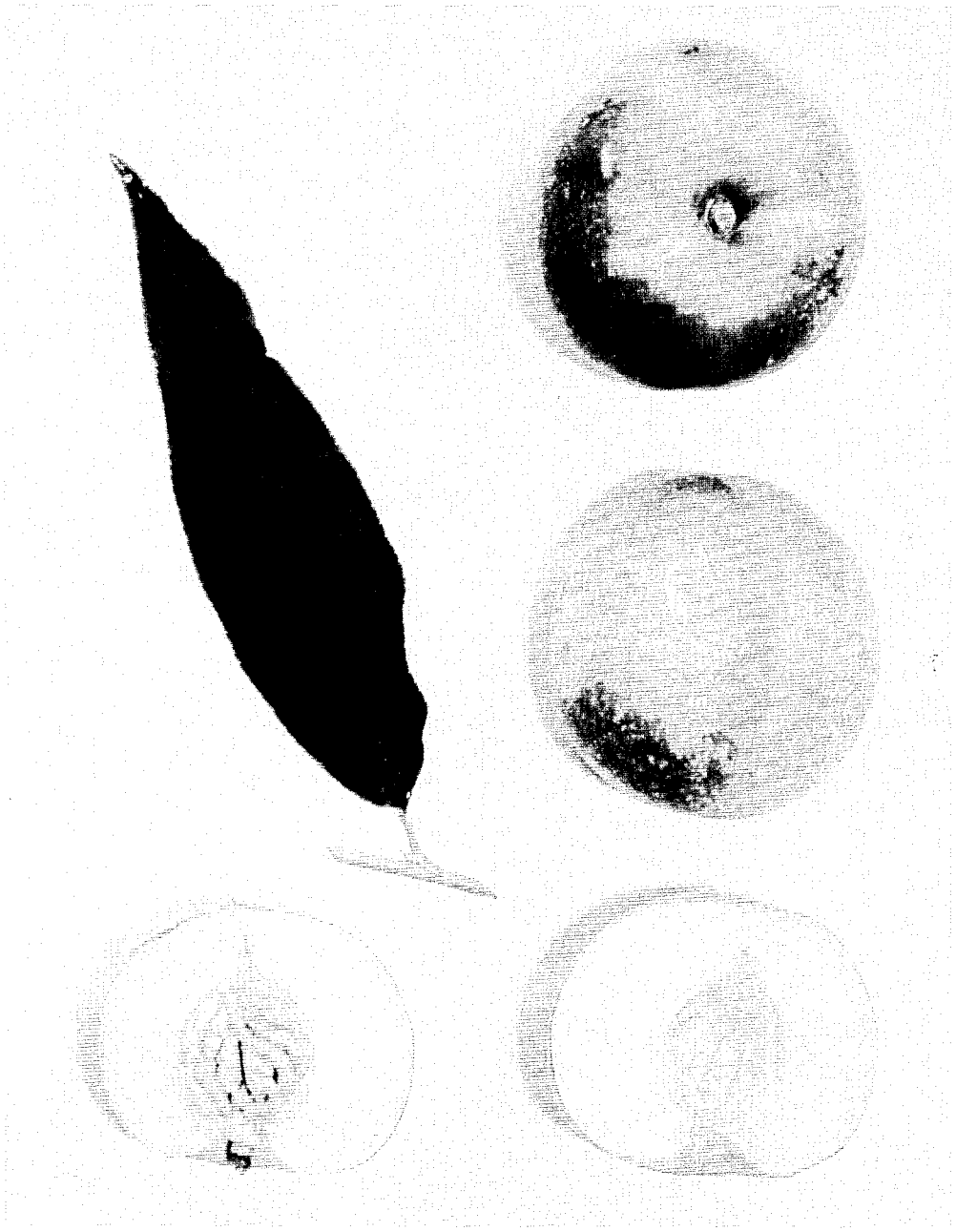
Inventor.
D. L. Armstrong
By: Robb & Robb
Attorneys.

United States Patent Office

Plant Pat. 2,958
Patented Dec. 23, 1969

2,958
NECTARINE TREE

David L. Armstrong, Ontario, Calif., assignor to Armstrong Nurseries, Inc., Ontario, Calif., a corporation of California Filed May 28, 1968, Ser. No. 732,787
Int. Cl. A01h 5/08
U.S. Cl. Plt.—41 1 Claim The present invention relates to a new and distinct variety of nectarine tree which was originated by me by crossing the nectarine variety known as "Panamint" (Plant Patent No. 1,100) with an unnamed and unpatented peach variety derived from a cross of the nectarine variety known as "Palomar" (Plant Patent No. 1,652) × the peach variety known as "Springtime" (Plant Patent No. 1,268), the variety "Panamint" being the seed parent and the unnamed variety being the pollen parent.

My new nectarine variety is one result of an extensive breeding program conducted by me with the objective of producing yellow-fleshed fruiting nectarine varieties, with the fruit having an early-ripening habit and being of good commercial quality. This objective was achieved in this new variety, along with other desirable features, as evidenced by the following unique combination of characteristics which are outstanding therein and which distinguish it from its parents, as well as from all other nectarine varieties of which I am aware:

(1) A vigorous tree habit, with a chilling requirement very nearly the same as that of "Springtime" peach (Plant Patent No. 1,268);

(2) Good fruit productivity;

(3) A fruit ripening period averaging about 11 to 13 days after "Mayred" nectarine (Plant Patent No. 2,758);

(4) A uniform ripening habit of the fruit;

(5) Smooth fruit skin, free of pubescence, typical of nectarines;

(6) Good fruit size for its relatively early ripening season, with the fruit being uniform in shape, nearly round and having no beak;

(7) A distinctive and attractive fruit skin color, said skin being heavily colored with dark red and with occasional mottling and flecking of yellow ground color showing through, particularly on the side away from the principal source of light;

(8) A significant absence of red color in the fruit flesh and particularly at the pit cavity, but with a minimal amount of red color being present in the flesh at the tree-ripe stage;

(9) An unusual and quite satisfactory free-stone fruit habit contrary to most early-ripening nectarines, with only a very small amount of flesh tending to cling to the stone as it separates from the flesh; and

(10) Excellent quality, texture and flavor of the fruit.

The seed parent, "Panamint," of my new variety is an early midseason ripening, yellow-fleshed nectarine, and its fruit tends to have more red color in the flesh, while the new variety is more properly considered as early-ripening and its skin color is more heavily pigmented, and has a tendency to be almost too heavily colored.

The unnamed pollen parent was a yellow-fleshed, free-stone peach which ripens in approximately the same season as the new variety and has about the same chilling requirement, whereas the new variety is mainly distinguished from this parent by being a nectarine instead of a peach.

As compared with its ancestor, "Palomar" nectarine, the new variety is distinguished therefrom by ripening nearly two months earlier.

In comparison with its ancestor, "Springtime" peach, the new variety is essentially distinguished therefrom by being a nectarine instead of a peach, and also by a later ripening habit.

The new variety most nearly resembles the nectarine variety known as "Merrill Sunrise" (Plant Patent No. 1,256 (which is characteristically russeted and has much less reddish pigment in the fruit skin than in the new variety, and requires more hours of winter chilling to bear satisfactory crops than does the new variety.

Asexual reproduction of my new variety by budding, as performed by me at Wasco, Calif., shows that the foregoing characteristics and distinctions come true to form and are established and transmitted through succeeding propagations.

The accompanying drawings shows typical specimens of the fruit and foliage of my new nectarine variety, with both exterior and sectional views of the fruit being shown, the latter exposing the stone in one half-section and the cavity in the other half-section, with all of the views being depicted in color as nearly true as it is reasonably possible to make the same in a color illustration of this character.

The following is a detailed description of my new variety, as based upon observation of specimens grown at Wasco, Calif., with color terminology in accordance with Robert F. Wilson's Horticultural Colour Chart (hereinafter abbreviated as (W) and Ridgway's Color Standards and Nomenclature (hereinafter abbreviated as (R)), except where general color terms of ordinary dictionary significance are obvious:

TREE

Habit: Vigorous; upright-spreading; fairly long internodes.

Chilling requirement: Moderate; seemingly very close to that of "Springtime" peach.

Fruit production: Has borne good crops consistently as long as observed at Wasco, Calif.

Current growth:

*Surface texture.*—Smooth; lenticels at first small and minute, but with age, some become larger, and sometimes raised toward the base, especially on the more vigorous shoots.

*Color.*—Greenish at first, overlaid with reddish-brown on surfaces exposed to most light, with lenticels appearing as near white dots; sometimes becoming brown with age.

Two-year wood:

*Surface texture.*—Moderately smooth, with slightly raised, somewhat irregular, longitudinal striations and numerous lenticels.

*Color.*—Greyish-brown.

Old wood:

*Surface texture.*—Moderately smooth, with numerous medium size to large, raised lenticels; some small longitudinal fissures.

*Color.*—Greyish-brown.

Leaves:
*Size.*—From 5½ inches to 7 inches long; from 1¼ inches to 1⅞ inches wide.
*Shape.*—Lanceolate; apex acuminate.
*Color (mature).*—Upper surface—near Deep Dull Yellow-Green (1). Plate XXXII (R). Undersurface—near Chrominum Green, Plate XXXII (R).
*Petiole.*—Medium length; medium thickness.
*Margins.*—Finely serrate; glandular.
*Glands.*—Mixed; mostly reniform; from small to medium size; usually 3 or 4 but sometimes 5 or 6 in number; borne both on the petiole and on the base of the leaf.

Vegetative buds:
*Size.*—Small.
*Shape.*—Pointed-ovoid.
*Scales.*—Pubescence short but thick.
*Color.*—Dark brown.

FLOWERS

Dates first and full bloom: Over several years of observation at Wasco, Calif., first bloom averaged from March 5 to March 8, and full bloom averaged from March 13 to March 18; averages about with "Springtime" peach.

Dormant flower buds:
*Shape.*—Ovoid.
*Scales.*—Pubescence thick; from moderate length to long.
*Color.*—Dark brown, but pubescence gives frosty appearance.

Size (when fully open): Showy; about 1½ inches in diameter.

Petalage: Single, usually 5 pedals.

Form: Cupped.

Color (open flower): Light pink.

FRUIT

Ripening dates: Begins to ripen on the average about June 6 or June 7, ranging from May 31 to June 16, which makes it average from 11 to 13 days after the beginning ripening period of "Mayred" nectarine.

Maturity when described: Soft tree-ripe.

Size: Averages large size.
*Axial diameter.*—From 2⅛ inches to 2¼ inches.
*Transverse diameter in suture plane.*—From 2½ inches to 2⅝ inches.
*Transverse diameter at right angles to suture plane.*—From 2⅜ inches to 2⅝ inches.

Form: Relatively uniform; globose; usually slightly compressed laterally toward suture.

Suture: Generally shallow; extending from base to apex, but discontinuous at apex; has slight depression beyond pistil point.

Ventral surface: Rounded; usually lipped throughout, with lips usually unequal.

Stem cavity: Usually rounded; sometimes elongated in suture plane, with suture showing on one side only.
*Depth.*—From ¼ inch to ⅜ inch.
*Width.*—From ⅝ inch to ¾ inch.

Base: From rounded to truncate.

Apex: Usually rounded; pistil point insignificant and sometimes non-existent.

Stem: From medium caliper to heavy; glabrous; weak adherence to stone. Length—approximately ¼ inch.

Skin:
*Thickness.*—Thin.
*Texture.*—Medium.
*Tenacity to flesh.*—Free.

*Pubescence.*—None; characteristic smooth skin of the nectarine.
*Color.*—Ground color varies from near Buttercup Yellow, Plate 5/2, page 5 (W) to near Saffron Yellow, Plate 7/2, page 108 (W) to near Garnet Brown, Plate 00918, page 192 (W).

Flesh:
*Quality.*—Medium firm; melting; fine texture.
*Aroma.*—Pronounced.
*Flavor.*—Good balance between sugar and acid; distinctive nectarine flavor.
*Color.*—Between Indian Yellow, Plate 6/2, page 6 (W) and Maize Yellow, Plate 607/1, page 69 (W), with surface of pit cavity between Lemon Yellow, Plate 4/2, page 4 (W) and Buttercup Yellow, Plate 5/2, page 5 (W).

Stone:
*Tenacity to flesh.*—Free; stone adheres to flesh only slightly along both dorsal and ventral edges.
*Size.*—From medium to large; from about 1¼ inches to 1⅜ inches long; from 1⅛ inches to 1¼ inches wide; from ⅞ inch to 1 inch thick.
*Form.*—Ovoid; cuneate toward apex.
*Base.*—Oblique.
*Hilum.*—Oblong; narrow.
*Apex.*—Acute.
*Sides.*—Usually equal and sometimes only slightly unequal; curved on right and left sides; irregularly furrowed toward apex; pitted toward base.
*Ventral edge.*—From medium thickness to thin; usually without wing toward base.
*Dorsal edge.*—Narrow; with deep, narrow groove to above center; ridges on either side interrupted.
*Color.*—Between Orange-Cinnamon, Plate XXIX (R) and Pinkish-Cinnamon, Plate XXIX (R).

I claim:

1. A new and distinct variety of nectarine tree of the yellow-fleshed, freestone and early-ripening fruit-bearing type, substantially as herein shown and described, characterized particularly as to novelty by the unique combination of a vigorous tree habit, with a chilling requirement very nearly the same as that of "Springtime" peach (Plant Patent No. 1,268), good fruit productivity, a fruit ripening period averaging about 11 to 13 days after "Mayred" nectarine (Plant Patent No. 2,758), a uniform ripening habit of the fruit, smooth fruit skin, free of pubescence, typical of nectarines, good fruit size for its relatively early ripening season, with the fruit being uniform in shape, nearly round and having no beak, a distinctive and attractive fruit skin color, said skin being heavily colored with dark red and with occasional mottling and flecking of yellow ground color showing through particularly on the side away from the principal source of light, a significant absence of red color in the fruit flesh and particularly at the pit cavity, but with a minimal amount of red color being present in the flesh at the tree-ripe stage, an unusual and quite satisfactory freestone fruit habit contrary to most early-ripening nectarines, with only a very small amount of flesh tending to cling to the stone as it separates from the flesh, and excellent quality, texture and flavor of the fruit.

No references cited.

ROBERT E. BAGWILL, Primary Examiner